United States Patent [19]

Okabe

[11] Patent Number: 5,216,133
[45] Date of Patent: Jun. 1, 1993

[54] HUMAN MONOCYTE GROWTH FACTOR

[75] Inventor: Tetsuro Okabe, Tokyo, Japan

[73] Assignee: Japan Antibiotics Research Association, Tokyo, Japan

[21] Appl. No.: 607,942

[22] Filed: Oct. 31, 1990

[30] Foreign Application Priority Data

Oct. 31, 1989 [JP] Japan .................................. 1-281974

[51] Int. Cl.$^5$ ...................... C07K 15/00; C07K 15/06
[52] U.S. Cl. .................................... 530/399; 530/324; 435/240.2; 435/240.25; 435/70.1; 436/63; 436/86; 436/68; 514/2; 514/21
[58] Field of Search ............................... 530/324, 399; 435/240.2, 70.1, 240.25; 436/63, 86, 68; 514/2, 21

[56] References Cited

U.S. PATENT DOCUMENTS 4,879,111 11/1989 Chong ................................ 424/85.5

FOREIGN PATENT DOCUMENTS 0140788 11/1979 Japan .

OTHER PUBLICATIONS

Journal of Cellular Biochemistry, vol. 40, No. 1, May 1, 1989, New York, pp. 193-199; S. M. Wahl et al.: "Role of Growth Factors in Inflammation and Repair".
Dinarello and Mier, "Lymphokines," *New Engl. J. Med.*, 317 (15):940-945 (1987).
Sieff, "Hematopoietic Growth Factors," *J. Clin. Invest.*, 79:1549-1557 (1987).
Metcalf, "The Molecular Control of Cell Division, Differentiation Commitment and Maturation in Haemopoietic Cells," *Nature* 339:27-30 (1989).
Ohta et al., "Induction of Proliferation of Human Circulating Monocytes In Vitro by Lectin-Induced Factor(s) from Lymphocytes," *Biochem. Biophys. Res. Commun.*, 126 (2):705-711 (1985).
Okabe et al., "A Human Monocyte Growth Factor Produced by Lung Cancer Cells," *Cancer Research*, 5:3863-3865 (1990).
Ohta et al., "1α,25-Dihydroxyvitamin $D_3$ (Calcitriol) Stimulates Proliferation of Human Circulating Monocytes In Vitro," *FEBS Letter*, 185 (1):9-13 (1985).
Kirkin Brewery KK, JA0140788, Nov. 1979, abstract in English language.
Clark et al., *Science*, 236, 1229-1237, 1987.

*Primary Examiner*—F. T. Moezie
*Attorney, Agent, or Firm*—Sughrue, Mion, Zinn, Macpeak & Seas

[57] ABSTRACT

A novel growth factor, human monocyte growth factor, stimulating proliferation and differentiation of human peripheral blood monocyte. The factor is a protein produced from human lung cancer cell line and having M.W. of about 21,000. The activity of the factor is heat-sensitive, trypsin-sensitive, chymotrypsin-sensitive, and destroyed by 2-mercaptoethanol. A purification process of the factor is also provided.

2 Claims, 6 Drawing Sheets

HUMAN MONOCYTE GROWTH FACTOR

BACKGROUND OF THE INVENTION

Field of the Invention

The present invention relates to a human monocyte growth factor for stimulating differentiation and proliferation of human peripheral blood monocyte, and a purification process for purifying the growth factor.

The hematopoietic progenitor cell is differentiated to be converted into cells having various functions. Such a cell is referred to as polyfunctional stem cell, and proliferation or differentiation thereof requires stimulation by specific proliferating factor or differentiating factor. It has been known in the art that the following four CSFs (colony stimulating factors) should be present for differentiating the hematopoietic progenitor cell to glanulocyte or macrophage. The first factor is a multi-CSF known as interleukin 3 (IL3) which promotes the proliferation of the granulocyte, macrophage and precursors thereof, and induces the differentiation of these cell linages. The second factor is granulocyte CSF (G-CSF) which promotes differantiation and/or proliferation of the granulocyte; the third factor is macrophage CSF (M-CSF) which differentiates and/or proliferates the macrophage; and the fourth factor is granulocyte-macrophage CSF (GM-CSF) which promotes proliferation of both of the granulocyte and macrophage cell lineages.

The structures and DNA sequence of these four CSF derived from mouse (mouse CSF) have already been clarified (Metcalf. S., Science, 229, 16, (1985); OKABE, Tetsuro et al., "IGAKU NO AYUMI" (Progress in Medicine), 135, 1037, (1985).) Most of the CSF derived from human being (human CSF) have functions and structures similar to those of mouse CSF. However, human M-CSF, which stimulates human macrophage has not yet been found. For example, the human M-CSF is homologous with the mouse-CSF and performs immunological cross reaction to exhibit a CSF activity to the mouse bone marrow cell. However, it does not exhibit CSF activity to the human bone marrow cell ("RINSHO KAGAKU" (Clinical Science), 22, 255, (1986); Dao. S. K. et al., Blood, 58, 630, (1981)).

On the other hand, although it had been commonly considered that the human peripheral blood monocytes were cells which did not divide or proliferate, the inventor found a humoral factor for proliferating and differentiating the human monocytes in a cultured medium in which lymphocytes stimulated by lectin were cultured. This study also shows that human peripheral blood monocytes can divide and/or proliferate. (Biochem. Biophys. Res. Commun., 125, 705–711, (1985)). The humoral factors found previously and reported by me in the reference as aforementioned are present in two fractions, respectively, each having a molecular weight of 25,000 and 60,000 in the conditioned medium of lymphocytes, and the activities thereof are partially absorbed by anti-M-CSF antibody or anti-GM-CSF. Accordingly, the soluble factors are present as a mixture of various soluble factors including M-CSF, GM-CSF and others, and the mechanisms thereof have not yet been made clear. However, it is estimated that the proliferation and differentiation of human monocytes are stimulated by the synergistic functions thereof.

Under such circumstances, I have found a novel proteinous factor which induces proliferation and differentiation of human peripheral blood monocytes in the conditioned medium of human cancer cell line, and succeeded to purify the same as a single substance. Further, the thus found human monocyte growth factor was isolated to investigate the physiological activity thereof to ascertain that it was a substance having a novel physiological activity which was different from those of the known CSF and γ-interferon. The human monocyte growth factor is expected to be used for a medicament for promoting the defensive action or reaction of the living body, into which the monocyte is participated; and thus it might be provided for an applications to exert various functions, including defensive action against infectious diseases, enhancement of immunological activities and enhancement of immunity against cancers by macrophage.

OBJECT AND SUMMARY OF THE INVENTION

The principal object of the present invention is to provide a novel physiologically active factor which promotes proliferation and differentiation of human monocytes.

The aforementioned object of the invention is achieved by the provision of a human monocyte growth factor which induces differentiation and/or proliferation of human monocyte.

The human monocyte growth factor, provided by the present invention, is a proteinous factor produced in a conditioned (or cultured) medium of human cancer cell line T3M-30Lu, the proteinous factor being heat-sensitive and sensitive to trypsin and having SH-sensitivity, and found to be a single substance which gives a single band in the SDS-polyacrylamide gel electrophoresis chart and has a molecular weight of about 21,000 daltons.

BRIEF DESCRIPTION OF THE DRAWINGS

FIGS. 7 to 9 are photographic images of human monocyte cells taken through a microscope, wherein

EMBODIMENT OF THE INVENTION

The present invention will now be described in detail by referring to some embodiments while taking in conjugation with the appended drawings showing the results of experiments.

Method of Measuring Monocyte Growth Factor

The activity of the monocyte growth factor (hereinafter indicated by abridgd simbol of "MoGF") was determined by monitoring the moitoic activity of the monocyte and the increment of the number of monocyte cells.

Human peripheral blood mononuclear cells were taken from bloods of healthy adults while using the Ficoll solution (P. Edelson and Z. A. Cohen, "In Vitro Methods in Cell Mediated and Tumor Immunity" (edited by B. R. Bloom and J. R. David), p333, (1976), Academic Press, New York).

The mononuclear cells are suspended in a Ham's F-10 medium (supplemented with 1% autologous serum), and incubated on a culture plate (Falcon 3047) at a density of $8 \times 10^5$ cells/well and incubated overnight in an incubator purged with 5% $CO_2$. Each well was then washed with F-10 medium to remove non-adherent cells. 95% or more of the cells adhering to respective wells are monocytes which is positive to α-naphtyl-butylate-estrase and exhibits phagocitic activity against latex particles.

The cells adhering to the wells were incubated in a 5% $CO_2$ incubator for 3 days. The used medium was the F-10 medium (supplemented with 1% autologous serum), and 10 μl for each of test samples were added to respective wells on the third day from the initiation of incubation.

On 4th day after the addition of the samples, the cells were pulse-labeled with 10 μl of $^3H$-thymidine (produced by New England Nuclear Corp.; Specific Activity = 6.7 μci/mmol) at a rate of 0.1 μci/well. After cultivating for 20 hours, the medium in each well was discarded, and then 1 ml of a 10% TCA (trichloro acetic acid) solution was added to each well and allowed to stand for 20 minutes. Then, the TCA solution was discarded and the TCA-insoluble fraction of the harvested cells was washed with methanol/ether (3:1) for two times, and 200 μl of a 1N NaOH solution was added and then allowed to stand at 37° C. for 60 minutes to solubilize the TCA-insoluble fraction. The solubilized fraction was neutralized with 200 μl of 1N HCl, added with 4.5 ml of scintillator (Aquazol-2), and then the radioactivity was measured by a liquid scintillation counter The incorporation of $^3H$-thymidine was taken as the criterion for the judgement on the DNA synthesizing capability or capacity, i.e. the miotoic activity, of the monocyte. All determinations were performed in triplicate cultures.

The number of monocyte cells were determined by counting the nuclei of the cells through the Nakagawa and Nathan Method (J. Immunol. Method, 56, 261, (1983)). In detail, under similar conditions for the aforementioned assay which are usually conducted to learn the incorporation of $^3H$-thymidine, human monocyte was incubated in a 5% $CO_2$ incubator at 37° C. and the cell numbers were determined daily. In determination of the cell number, after the removal of the medium a 1% Cetavlon (produced by Daiichi Pharmaceutical Co., Ltd.) and 0.2% citric acid solution were added to the culture wells, followed by treatment for 20 minutes, and then the cell nuclei were set afloat by pipetting. The floated nuclei were counted with a hemocytometer under a phase contrast microscope to know the cell number.

Culture of T3M-30Lu Cell

The human lung cancer cell line T3M-30Lu established by me, the inventor, from large cell carcinoma of the lung was cultured. The cell line had been successively passage-cultured over a period of 4 years in F-10 medium supplemented with 10% fetal bovine serum (FBS) in my laboratory. And it has been found that the very cell line produces the human monocyte growth factor of the invention. (The cell has been deposited with the Fermentation Research Institute (FRI), Agency of Industrial Science and Technology, Ministry of International Trade and industry, Japan, with the Accession No. FERM BP-3120; Deposition Date: Oct. 21, 1989, Depositary: JAPAN ANTIBIOTICS RESEARCH ASSOCIATION of 20-8, Kamiosaki, 2-chome, Shinagawa-ku, Tokyo, 141, JAPAN).

The T3M-30Lu cell cultured in a plastics culture flask was grown rapidly to form a monolayer which adhered onto the wall of the flask. The monolayer cells were removed from the wall of the culture flask by trypsinization, and then subcultured in a fresh medium to be successively propagated. Normally, an F-10 medium (containing 10% FBS and antibiotics) is used for culture.

In purification of the monocyte growth factor of the invention, the T3M-30Lu cell, was transferred to a serum-free medium, and the filtrate of the cultured medium was used as a raw material. In detail, after the T3M-30Lu cell was cultured to achieve confluent growth in the aforementioned F-10 medium supplemented with 10% FBS, the culture medium was replaced by a serum-free medium (F-10 medium containing 200 mg/ml dimethyl-β-cyclodextrin). Cells may be grown slowly in this serum-free medium. The culture medium was replaced by a fresh serum-free medium at every one week intervals, and the conditioned mediums were collected to be used as the raw material from which purified growth factor of the invention was extracted.

The increase of human monocyte cells due to an addition of each conditioned medium were monitored by the determination method as described above. The results were that monocytes exposed to the control conditioned medium alone decreased in cell number by about 30%, whereas monocytes exposed to the conditioned medium of T3M-30Lu increased in cell number by about 300%. Meanwhile, although investigations were made on various cultured mediums in which other cancer cell lines, such as K-562, HL-60, KG-1, HeLa, T-24, T3M-1, T3M-3 and HLC-1, were cultured, similar MoGF activity analogous to that found when the human lung cell line T3M-30Lu was cultured through the aforementioned culture system was not observed.

Figure 1:
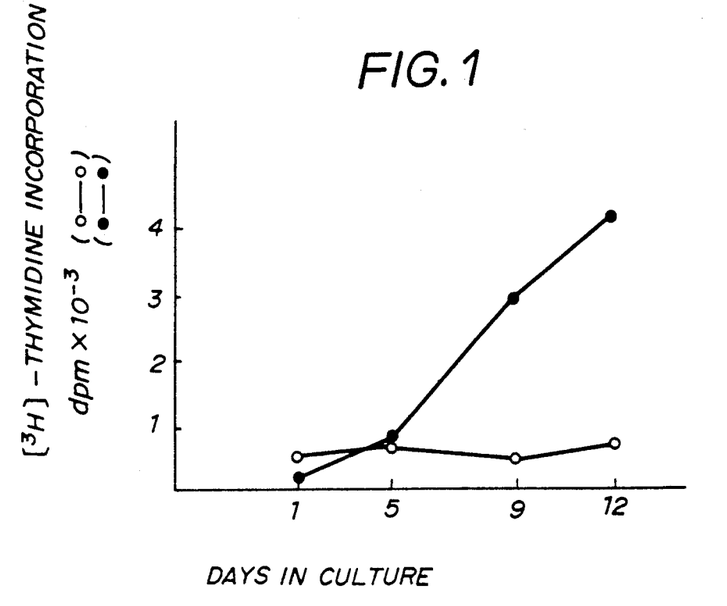
FIG. 1 is a graph showing the change in incorporation of $^3$H-thymidine by the human monocytes in terms of the lapse of time after the conditioned medium of T3M-30Lu is added.

The MoGF activity of the filtrate of the cultured medium was investigated by means of the determination of $^3H$-thymidine incorporation of human monocyte, following the aforementioned assaying system. As shown in FIG. 1, incorporation of $^3H$-thymidine revealing proliferation of human monocyte was observed after the third day from the addition of the filtrate of T3M-30Lu cell culture medium (shown in the line — —). In the same Figure, the line —◯— shows the result of a control in which a serum-free medium usually used for the T3M-30Lu cell culture was used.

Figure 2:
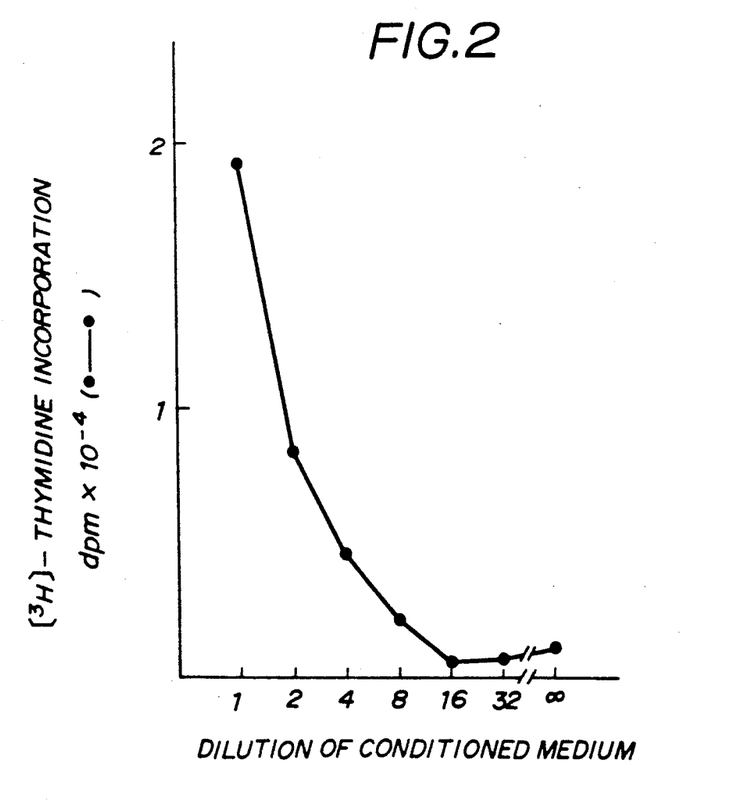
FIG. 2 is a graph showing the concentration dependency of the conditioned medium of T3M-30Lu in terms of the $^3$H-thymidine incorporation by the human monocytes.

FIG. 2 shows the dose response in terms of the $^3H$-thymidine incorporation of the conditioned medium of T3M-30Lu. As shown, the MoGF activity was detected even when the conditioned medium was diluted 4-fold to 8-fold.

Purification of Human Monocyte Growth Factor

The conditioned medium of T3M-30Lu cell cultivation was collected, and the thus collected medium was filtered through a Hollow Fiber Filter SEP-1013 (Asahi Chemical Industry Co., Ltd.; Molecular Weight Cut Off of 3,000) to remove low molecular weight ingredients to be concentrated as high as 50-fold as that of the conditioned medium.

The concentrated culture medium was fractionated by salting out with ammonium sulfate at pH 7.5. The precipitates corresponding to the 30 to 60% saturation of $(NH_4)_2SO_4$ fraction were collected by centrifugation (35,000 g, 30 minutes). After dissolving the precipitate in 50 mM Tris-HCl (pH 7.5), the resultant suspension was subjected to centrifugation to remove insoluble materials, and the supernatant left after centrifugation was subjected to ultrafiltration through HI-15P Filter (produced by Asahi Chemical Industry Co., Ltd.) to be concentrated 20-fold.

Figure 3:
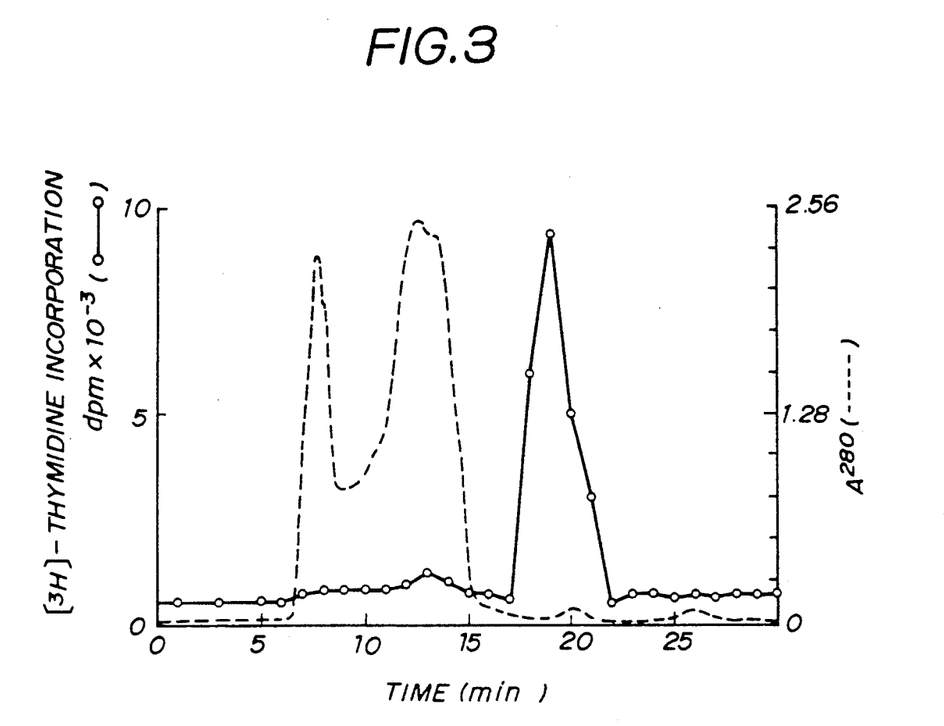
FIG. 3 is a chart showing the elution pattern of Superose 12 column chromatography.

200 μl of the concentrated solution was subjected to gel filtration through Superose 12 column (HR 10/30, Pharmacia P-L Biochemicals). The column was loaded on the FPLC apparatus (Fast Performance Liquid Chromatography; produced by Pharmacia P-L Biochemicals), and 50 mM Tris-HCl (pH 7.5) was flown through the column at a flow rate of 1 ml/min. The eluate was fractionated by every 1 ml, and MoGF activities of every fractions were determined. As shown in FIG. 3, a peak showing $^3H$-thymidine incorporation was observed at a position corresponding to a molecular weight of about 16,000.

Figure 4:
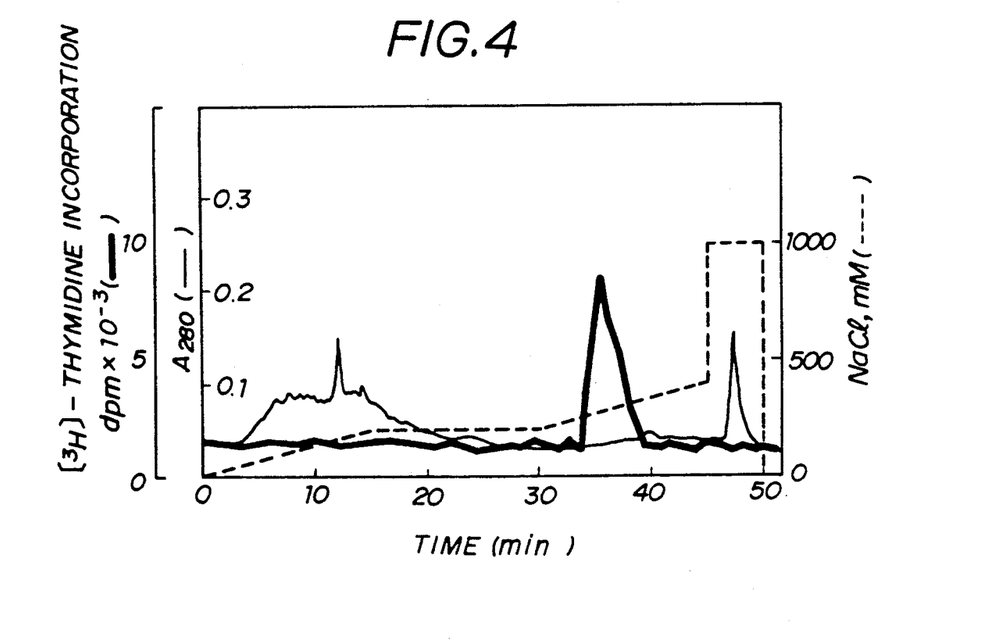
FIG. 4 is a chart showing the elution pattern of mono-Q column chromatography.

That active fraction was pooled, insoluble ingredients therein being removed by centrifugation (35,000g, 30 minutes at 4° C.), and then the fraction was directly applied to a Mono-Q Column (HR 5/5, produced by Pharmacia P-L Biochemicals) to be subjected to ion exchange chromatography. The column was eluted with 50 mM Tris HCl (PH 7.5) at a flow rate of 1 ml/minute, and at a linear concentration gradient from the time of initiation of elution until the lapse of 15 minutes being in the range of 0 to 200 mM NaCl, from the lapse of 15 minutes until the lapse of 30 minutes being 200 mM NaCl, and at a linear concentration gradient from the lapse of 30 minutes until the lapse of 45 minutes being in the range of 200 to 400 mM NaCl. As shown in FIG. 4, a single peak showing $^3H$-thymidine incorporation was observed at the fraction eluted by about 280 mM NaCl. The influence of the active fraction on the human monocyte was investigated, in accordance with the aforementioned procedure. The result was that the number of cells in the active fraction was increased by about 2.3 times as that found in the control.

TABLE 1

|  | Number of Human Monocyte Cell Nuclei |
|---|---|
| Active Fraction | $1.6 \times 10^5$ |
| Control | $0.7 \times 10^5$ |

Figure 5:
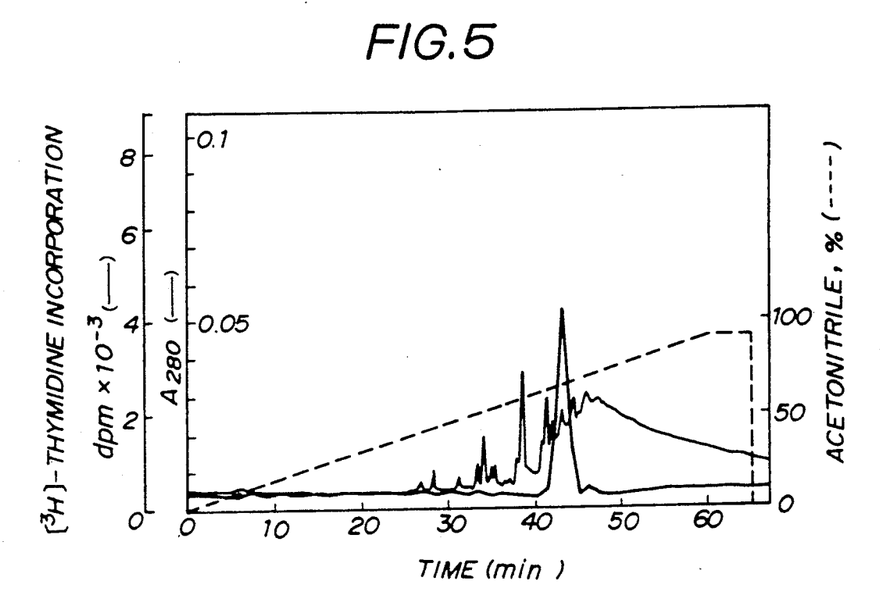
FIG. 5 is a chart showing the elution pattern obtained by a reversed phase HPLC.

Then, the active fraction was further purified by reversed phase HPLC. The active fraction of the Mono-Q-column was directly applied to the Vydac $C_4$ column (4.6×250 mm; produced by The Separation Group) loaded on the HLC-803D HPLC system produced by Toyo Soda Manufacturing Co., Ltd. After flowing 0.1% trifluoroacetic acid (TFA) for 10 minutes to wash the column, the fraction was eluted with a linear concentration gradient of 0 to 90% acetonitrile in 0.1% TFA for 30 minutes and at a flow rate of 0.5 ml/minute to fractionate by every one ml. The result are shown in FIG. 5. As shown, a single peak showing $^3H$-thymidine incorporation was found at the fraction eluted by 65% acetonitrile. That fraction was collected and dialyzed, and then analyzed through SDS polyacrylamide gel electrophoresis, whereby a single band was found at a position corresponding to a molecular weight of about 21,000.

Characteristic Features of Human Moncyte Growth Factor

The thus isolated human monocyte growth factor was subjected to themal treatment, treatment with trypsin, treatment with chymotrypsin and treatment with 2-mercaptoethanol to learn the stabilities thereof in these treatments. The treatment with trypsin was performed by incubating the samples with 50 U/ml insolubilized trypsin (Produced by Sigma) for a predetermined time period, and then the insolubilized trypsin was removed by centrifugation to stop reaction. The treatment by chymotrypsin was performed by incubating the samples with chymotrypsin (20 μg/ml; Specific Activity = 50 U/mg; Sigma) in a 0.05 M Tris HCl buffer (pH 7.5) at 37° C. for 2 hours. The treatment with 2-mercaptoethanol was performed by treating the samples with 0.5% 2-mercaptoethanol at room temperature for 60 minutes. After the completion of respective treatments, each of the samples was diluted with PBS (containing 1 mg/ml of BSA) to have a twice volume as large as that immediately after each treatment, and then subjected to desired assay. The results are shown in Table 2.

TABLE 2

| Stability of Human Monocyte Growth Factor | |
|---|---|
|  | Activity for Uptaking $^3H$-Thymidine (% control) |
| Control | 100 |
| Heat Treatment |  |
| 25° C., 4 hours | 80.9 |
| 56° C., 60 minutes | 75.4 |
| 100° C., 10 minutes | 6.4 |
| Treatment with Trypsin |  |
| 37° C., 120 minutes | 40.7 |
| 37° C., 240 minutes | 26.9 |
| Treatment with Chymotrypsin |  |
| 120 minutes | 2.1 |
| 120 minutes | 1.8 |
| Treatment with 2-mercaptoethanol 60 minutes | 2.4 |

From the results shown in Table 2, it was found that the human monocyte growth factor of the invention was estimated to be a protein which was heat labile and sensitive to trypsin and chymotrypsin, and that it had at least one S-S linkage affecting the MoGF activity from the result that it showed SH-sensitivity.

The amino acid composition of the MoGF was found from the amino acid analysis conducted as follows. Amino acid analysis of the protein hydrolysate was carried out on a Waters automatic amino acid analyzer. Proteins (1 ug for each) were hydrolyzed in 0.5 ml of 6N HCl at 110° C. for 24 hours in an evacuated, sealed tubes. The amino acid compositions of purified proteins are shown in Table 3. The compositions were extremely rich in hydrophobic residues, Leu, Ile, and Val, where the summation of these residues reached 24%.

TABLE 3

| Lys | 10.5 |
|---|---|
| His | 3.0 |
| Arg | undetectable |
| Asp + Asn | 3.6 |
| Thr | 5.1 |
| Ser | 7.4 |
| Glu + Gln | 11.2 |
| Pro | 8.4 |
| Gly | 8.5 |
| Ala | 6.0 |
| Cys | 0.6 |
| Val | 7.3 |
| Met | 2.1 |
| Ile | 6.4 |
| Leu | 10.4 |
| Tyr | 4.3 |
| Phe | 5.4 |
| Trp | undetectable |

Figure 6:
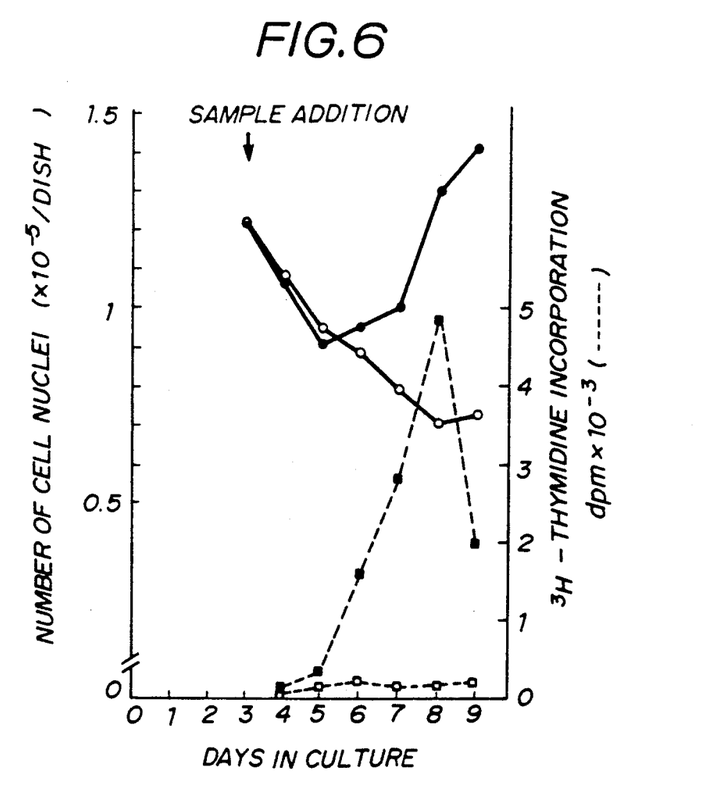
FIG. 6 is a graphical representation showing the growth promoting effect of purified MoGF on the human monocyte cell.

In addition, the human monocyte growth factor of the invention was added to human monocyte cells on three days after the initiation of culture, and the change in cell number and DNA synthesis were investigated (see FIG. 6). Although the number of cells of control culture without MoGF was normally decreased as shown by the plot (—○—), increase of cell number in culture with MoGF was observed after 3rd day (6th day from the initiation of culture) from the addition of MoGF as shown by the plot (— —). In addition, whereas the control culture (—□—) exhibited negligible DNA synthesizing capacity, marked DNA synthesis was observed after the 2nd day (5th day from the initiation of culture from the addition of MoGF when MoGf was added (— —).

Figure 7:
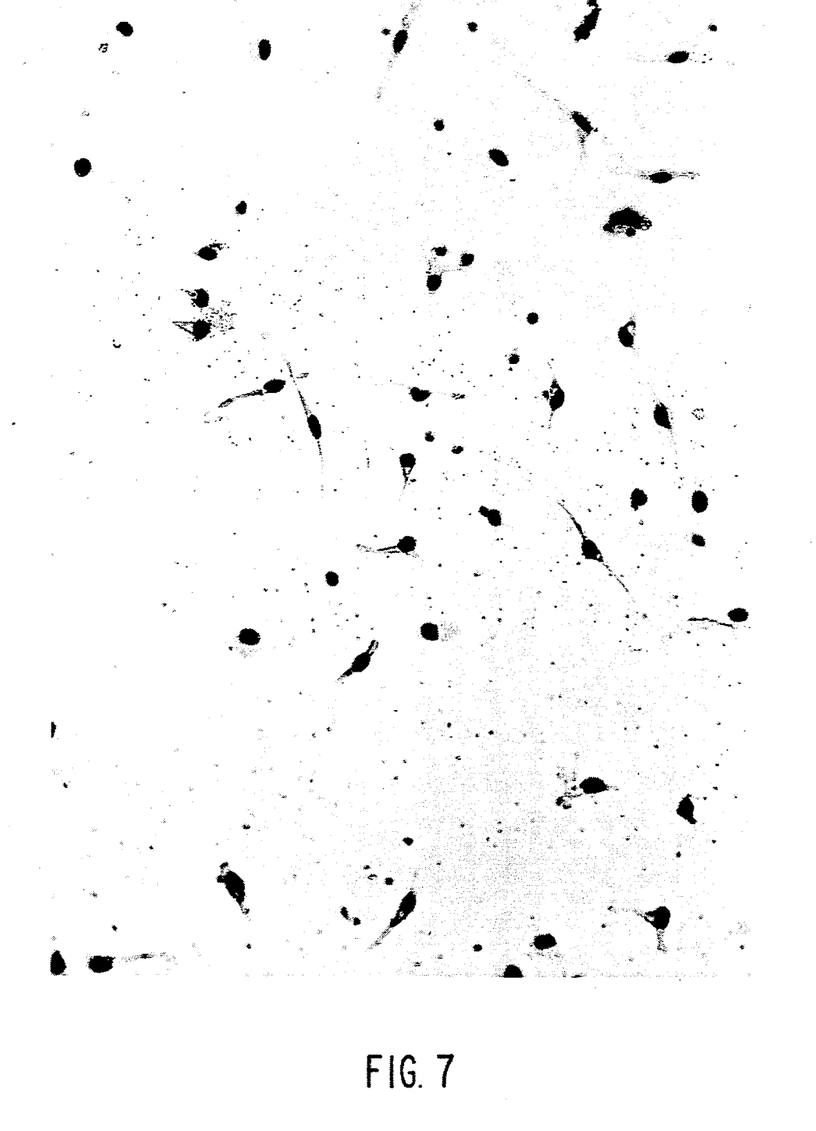
FIG. 7 shows a photographical image of a control and FIGS. 8 and 9 show photographic images of the cells when MoGF is added.
Figure 8:
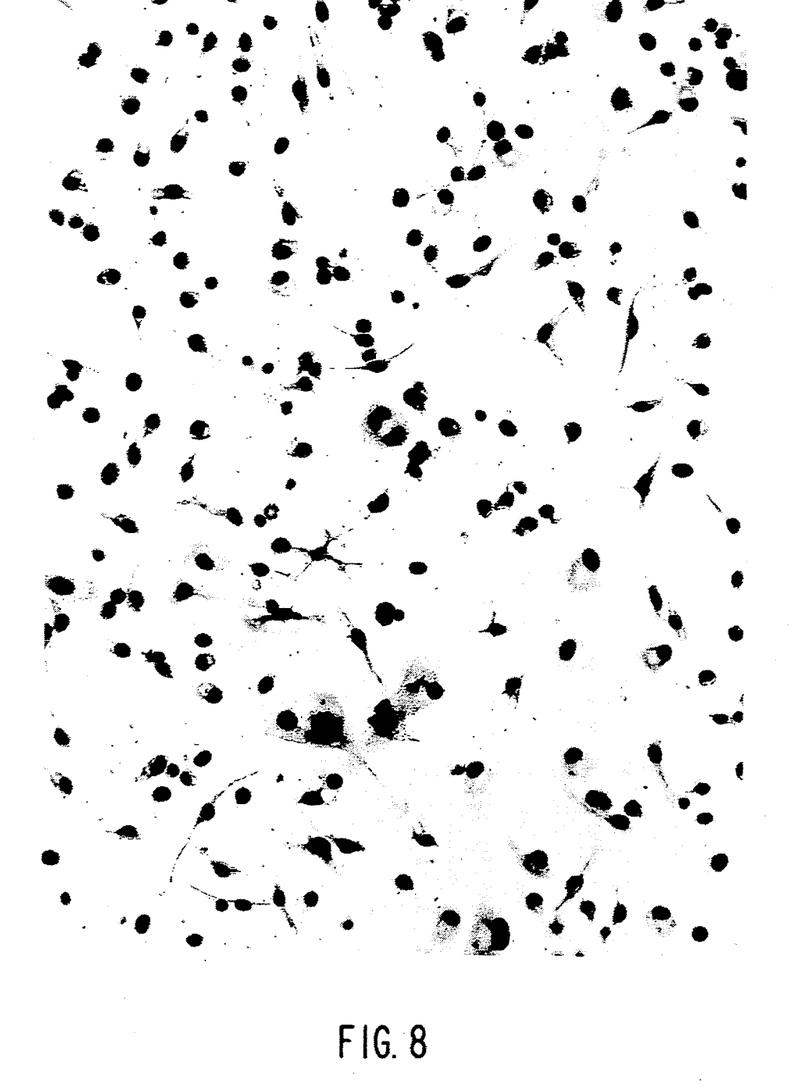
Figure 9:
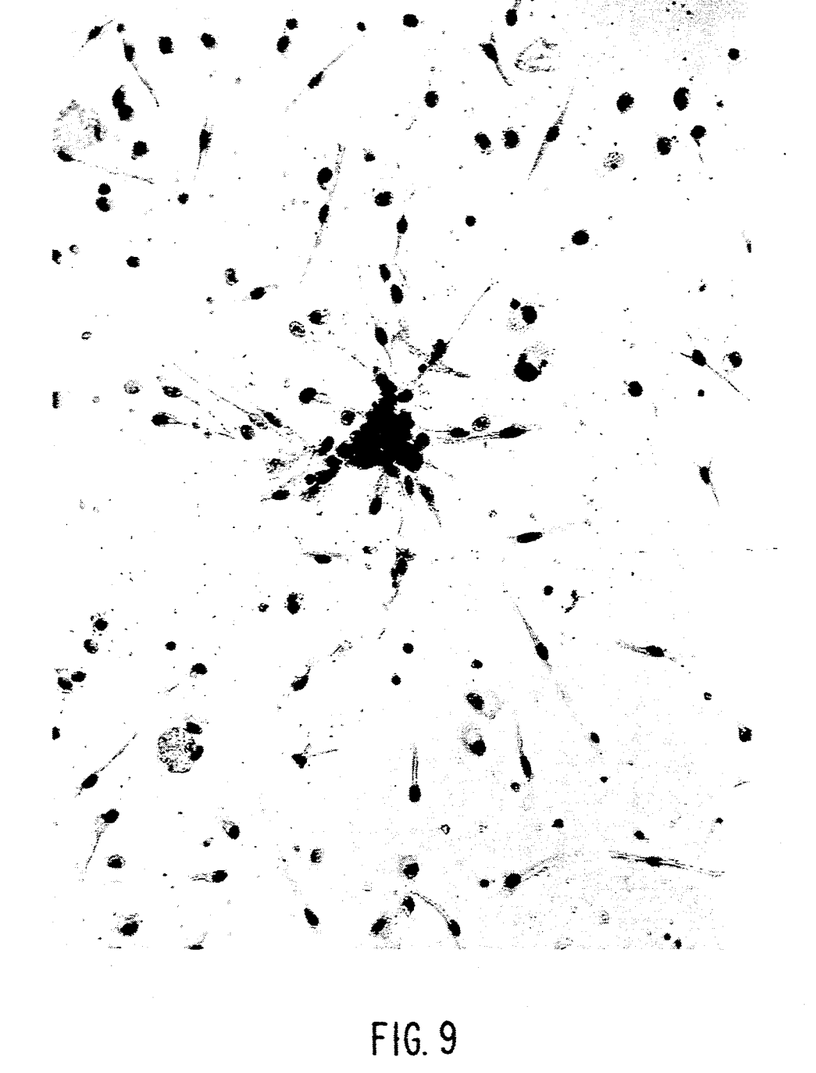

Furthermore, the morphological change of the human monocyte by the addition of MoGF of the invention was examined through a microscope. As compared to the control (FIG. 7; 8th day of culture), the human monocyte cells were increased in size by the addition of MoGF with the increase in size of the cytoplasm (FIG. 8; 5th day after the addition of MoGF). A cluster of human monocytes was observed in a different view field (FIG. 9). The cluster was analogous to those observed when monocytes or macrophages attacked foreign invaders. In view of the result that such cluster was formed by the addition of MoGF even when any foreign invaders was not present, it was expected that the MoGF of the invention not only promoted proliferation of human monocytes but also induced differentiation of the human monocytes to be ready for immediate response for initiating living body defensive actions. Accordingly, the MoGF of the invention may be used as various medicines, in wide application ranges, for promoting or enhancing defensive actions by the living body, into which monocytes are participated, for example, promoting cellular immunne functions or promoting immunity against cancers to which macrophages are participated.

Meanwhile, the active fraction of Superose 12 column chromatography was further investigated, following ordinary process in which the colony method was adopted, in order to investigate the influences of MoGF on human and mouse bone marrow cells. However, no CSF activities were found for both bone marrow cells. Those facts revealed that the MoGF of the invention was different from the known CSF.

It has been recently reported that the macrophage activating factor (MAF) for activating cytotoxicity of monocyte-macrophage against the tumor cells is immunologically identical to the γ-interferon. In view of the above, the active fraction from Superose 12 column chromatography was used to examine the interferon activity of MoGF. Generally in accordance with the usually employed method (Nature, 295, 503, (1982); Celluler Immunol., 49, 390, (1980)), the interferon activity thereof was examined while using FL cells derived from human amnion and Sindbis virus to reveal that the active fraction of MoGF had no interferon activity. Likewise, the active fraction of Superose 12 column chromatography exerted no immunological reactivity with the anti- γ-interferon antibody. It was also ascertained that γ-interferon per se had no MoGF activity. As should be appreciated from the foregoing, it has been confirmed that MoGF provided by this invention is utterly a novel physiologically active substance which is clearly different from γ-inteferon.

As has been described in detail hereinbefore, the human monocyte growth factor of the invention is a novel physiologically active material which is distinctive from the known CSF and γ-interferon, and has functions of inducing and/or promoting proliferation and differentiation of human monocytes. Accordingly, the human monocyte growth factor of the invention may be used for various applications for promoting defense actions by the living body into which monocytes are participated.

What is claimed is:

1. A substantially pure human monocyte growth factor derived from a human lung cancer cell line for stimulating differentiation and proliferation of human monocytes, wherein said human monocyte growth factor is sensitive to heat, trypsin and chymotrypsin, has an SH-sensitivity, and has a molecular weight of about 21,000 daltons on SDS-polyacrylamide gel electrophoresis.

2. The human monocyte growth factor as claimed in claim 1, wherein said human lung cancer cell line is T3M-30Lu.

* * * * *